US012673187B2

(12) United States Patent
Fujii

(10) Patent No.: US 12,673,187 B2
(45) Date of Patent: Jul. 7, 2026

(54) FLEXIBLE MANIPULATOR

(71) Applicant: OLYMPUS MEDICAL SYSTEMS CORP., Tokyo (JP)

(72) Inventor: Yuta Fujii, Inagi (JP)

(73) Assignee: Olympus Medical Systems Corp., Tokyo (JP)

( * ) Notice: Subject to any disclaimer, the term of this patent is extended or adjusted under 35 U.S.C. 154(b) by 860 days.

(21) Appl. No.: 17/959,854

(22) Filed: Oct. 4, 2022

(65) Prior Publication Data

US 2023/0121140 A1 Apr. 20, 2023

Related U.S. Application Data

(60) Provisional application No. 63/255,989, filed on Oct. 15, 2021.

(51) Int. Cl.
| | |
|---|---|
| *A61B 17/29* | (2006.01) |
| *A61B 17/00* | (2006.01) |
| *A61B 90/00* | (2016.01) |
| *A61M 25/01* | (2006.01) |
| *A61M 25/09* | (2006.01) |

(52) U.S. Cl.
CPC .. *A61M 25/09033* (2013.01); *A61M 25/0136* (2013.01); *A61M 25/0147* (2013.01)

(58) Field of Classification Search
CPC ......... A61M 25/09033; A61M 25/0136–0147; A61B 2017/00318–00331; A61B 2017/2927–293
See application file for complete search history.

(56) References Cited

U.S. PATENT DOCUMENTS

| | | | | |
|---|---|---|---|---|
| 5,813,290 | A * | 9/1998 | Takahashi | F16C 1/223 |
| | | | | 74/501.5 R |
| 6,547,757 | B1 * | 4/2003 | Kranz | A61B 5/6886 |
| | | | | 600/478 |
| 10,864,053 | B2 | 12/2020 | Hasegawa et al. | |
| 2008/0262537 | A1 * | 10/2008 | Lee | A61B 17/29 |
| | | | | 606/205 |

(Continued)

FOREIGN PATENT DOCUMENTS

| | | | | |
|---|---|---|---|---|
| EP | | 2403421 B1 * | 7/2019 | A61B 17/29 |

*Primary Examiner* — Matthew Kremer
*Assistant Examiner* — Aaron Merriam
(74) *Attorney, Agent, or Firm* — Morgan, Lewis & Bockius LLP

(57) ABSTRACT

A flexible manipulator includes an insertion portion including a tubular flexible portion, a bending portion, and a distal end portion. The flexible manipulator includes an operating unit on a proximal end side of the insertion portion, the operating unit including a first operating portion. The flexible manipulator includes a tube inside the tubular flexible portion, the tube including a through-hole spirally extending along a longitudinal axis of the tube from a proximal end to a distal end. The flexible manipulator includes a wire extending through the through-hole, a first end of the wire connected to the distal end portion and a second end of the wire connected to the first operating portion. The flexible manipulator includes an adjustment mechanism. The bending portion is a tubular body between the distal end portion and a distal end side of the tube.

25 Claims, 10 Drawing Sheets

(56)          References Cited

U.S. PATENT DOCUMENTS

| | | | |
|---|---|---|---|
| 2011/0144430 A1* | 6/2011 | Spivey | A61B 1/00042 |
| | | | 600/106 |
| 2018/0296801 A1* | 10/2018 | Tegg | A61M 25/0012 |
| 2019/0029767 A1* | 1/2019 | Hasegawa | A61B 34/30 |

* cited by examiner

FIG.2

FLEXIBLE MANIPULATOR

RELATED APPLICATION DATA

This application is based on and claims priority under 35 U.S.C. § 119 to U.S. Application No. 63/255,989 filed on Oct. 15, 2021, the entire contents of which are incorporated herein by reference.

FIELD OF THE DISCLOSURE

The present disclosure relates to a flexible manipulator.

BACKGROUND

U.S. patent Ser. No. 10/864,053 B2 discloses a flexible manipulator that employs a so-called twisted multi-lumen tube as a long tube through which a wire used for bending a distal end portion is inserted.

Specifically, the twisted multi-lumen tube is provided with an inner hole spirally extending along the longitudinal axis of the twisted multi-lumen tube. The wire is inserted through the inner hole.

BRIEF SUMMARY OF EMBODIMENTS

A flexible manipulator includes an insertion portion including a tubular flexible portion, a bending portion, and a distal end portion. The flexible manipulator includes an operating unit on a proximal end side of the insertion portion, the operating unit including a first operating portion. The flexible manipulator includes a tube inside the tubular flexible portion, the tube including a through-hole spirally extending along a longitudinal axis of the tube from a proximal end to a distal end. The flexible manipulator includes a wire extending through the through-hole, a first end of the wire connected to the distal end portion and a second end of the wire connected to the first operating portion. The flexible manipulator includes an adjustment mechanism. The bending portion is a tubular body between the distal end portion and a distal end side of the tube. Operation of the first operating portion transmits a force applied to the first operating portion via the wire to the distal end portion to bend the bending portion relative to a central axis of the insertion portion. The adjustment mechanism adjusts a tension in the wire.

BRIEF DESCRIPTION OF THE DRAWINGS

FIG. 2 is a diagram illustrating an access device.

DETAILED DESCRIPTION

Figure 1:
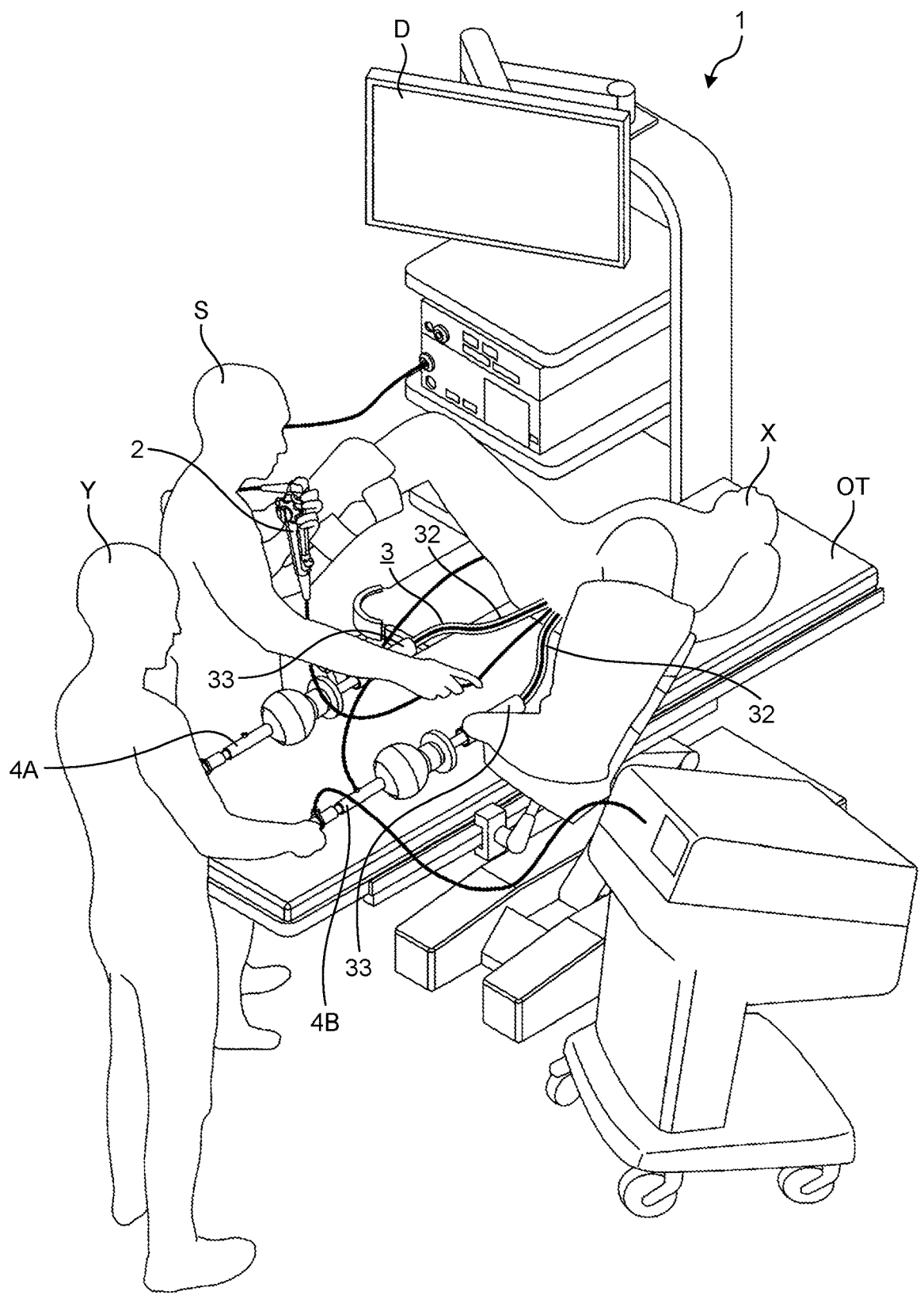
FIG. 1 is a diagram illustrating a medical manipulator system according to a first embodiment.

Modes for carrying out the present disclosure (hereinafter, embodiments) will be described below with reference to the drawings. Note that the present disclosure is not limited to the embodiments described below. Further, in the description of the drawings, the same portions are denoted by the same reference numerals.

First Embodiment

[Configuration of Medical Manipulator System]

FIG. 1 is a diagram illustrating a medical manipulator system 1 according to a first embodiment.

The medical manipulator system 1 is a system for treating a living tissue in a body cavity by two flexible manipulators 4A and 4B while observing an endoscopic image in the body cavity of a patient X captured by an endoscope 2 operated by a scopist S and displayed on a display D. As illustrated in FIG. 1, the medical manipulator system 1 includes an access device 3 which is inserted into a body cavity together with the endoscope 2, and two flexible manipulators 4A and 4B which are inserted into the body cavity while being guided by the access device 3.

Note that FIG. 1 illustrates a state in which the endoscope 2, the access device 3, and the two flexible manipulators 4A and 4B are inserted into the body cavity from the anus of the patient X on the operating table OT.

Figure 2:
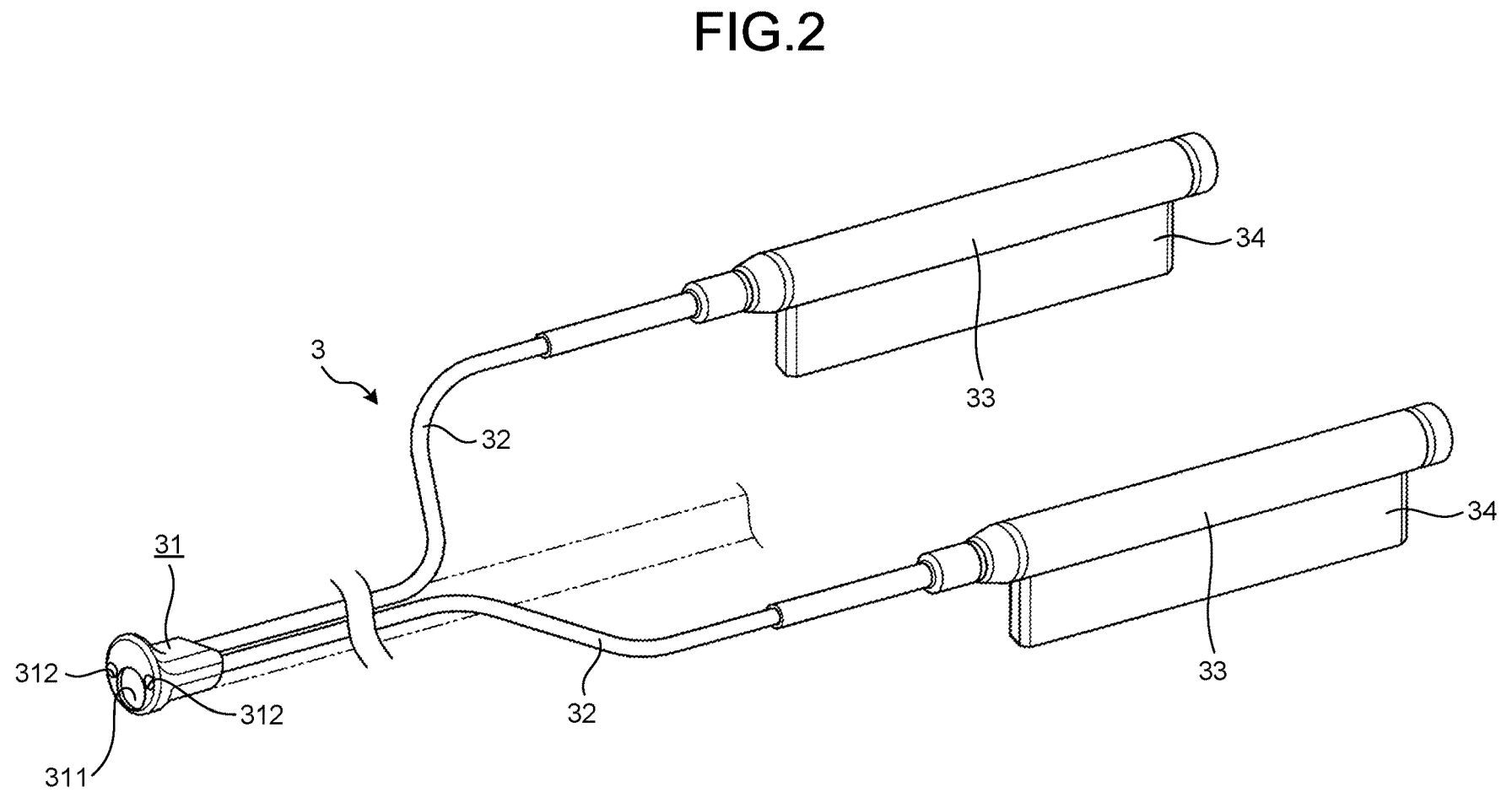

FIG. 2 is a diagram illustrating the access device 3.

As illustrated in FIG. 2, the access device 3 includes an endoscope mounting portion 31, two flexible tubes 32, and two rigid tubular portions 33.

The endoscope mounting portion 31 is a portion to which the distal end portion of the endoscope 2 is mounted. As illustrated in FIG. 2, the endoscope mounting portion 31 has a columnar shape, and has a first mounting hole 311 and two second mounting holes 312 each penetrating from the proximal end to the distal end along the central axis of the column. The endoscope 2 has a distal end portion mounted in a state of being inserted through the first mounting hole 311. The two flexible tubes 32 each have distal end portions mounted in a state of being inserted through the two second mounting holes 312, respectively.

The flexible tube 32 is a long tube having flexibility.

The rigid tubular portion 33 is a tubular body formed of a rigid member, and has a distal end connected to the proximal end portion of the flexible tube 32. The rigid tubular portion 33 communicates with the flexible tube 32. The rigid tubular portion 33 is provided with a fixing portion 34 for fixing the rigid tubular portion 33 to the operating table OT.

The two flexible manipulators 4A and 4B are devices operated by a surgical operator Y (FIG. 1) and have substantially the same configuration. Therefore, only the configuration of the flexible manipulator 4A of the two flexible manipulators 4A and 4B will be described below.

[Configuration of Flexible Manipulator]

Figure 3:
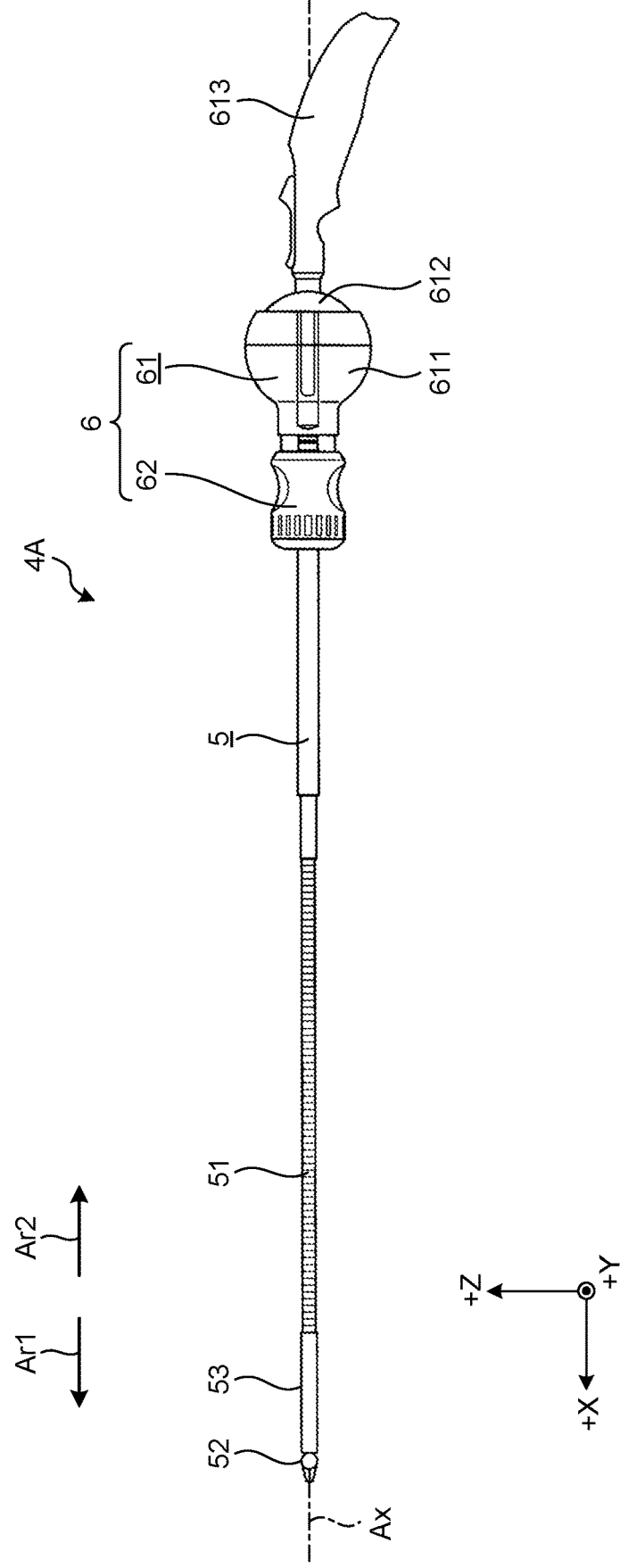
FIG. 3 is a diagram for explaining a configuration of a flexible manipulator.
Figure 4:
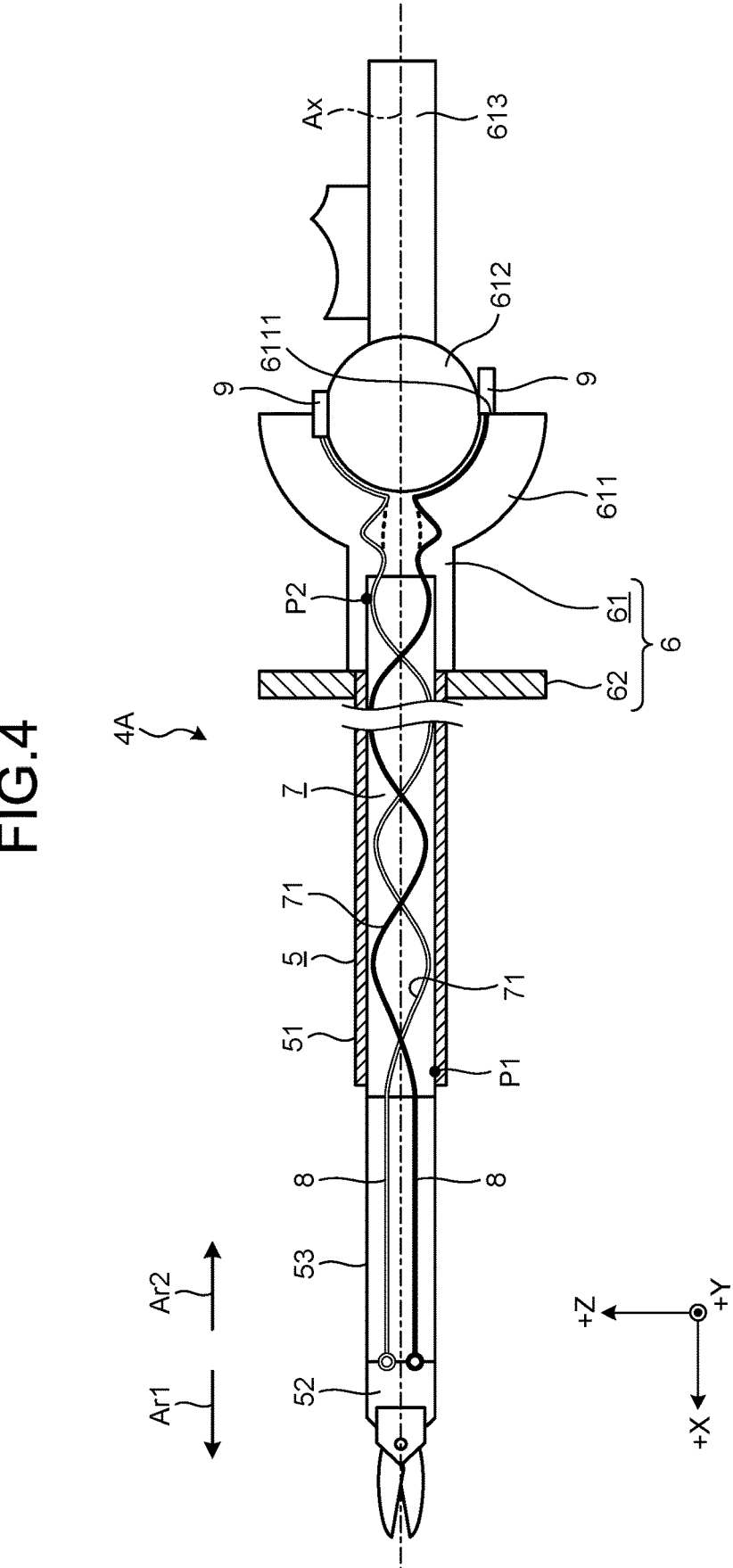
FIG. 4 is a diagram for explaining the configuration of the flexible manipulator.

FIGS. 3 and 4 are diagrams for explaining the configuration of the flexible manipulator 4A. In particular, FIG. 3 is a diagram illustrating an external configuration of the flexible manipulator 4A. FIG. 4 is a diagram schematically illustrating an internal configuration of the flexible manipulator 4A.

Note that, In the following description of the configuration of the flexible manipulator 4A, the XYZ-coordinate axes of the X-axis, the Y-axis, and the Z-axis orthogonal to each other are used. The X-axis is an axis parallel to the central axis Ax (FIGS. 3 and 4) of a flexible portion 51. The Y-axis is an axis orthogonal to the plane of the page of FIG. 1. The Z-axis is an axis along the vertical direction in FIG. 1. In the following, one side (+X-axis side) along the central axis Ax is referred to as a distal end side Ar1 (FIGS. 3 and 4), and the other side (−X-axis side) is referred to as a proximal end side Ar2 (FIGS. 3 and 4).

As illustrated in FIG. 3 or 4, the flexible manipulator 4A includes an insertion portion 5, an operating unit 6, a tube 7 (FIG. 4), a wire 8 (FIG. 4), and an adjustment mechanism 9 (FIG. 4).

The insertion portion 5 is a portion that is inserted through the rigid tubular portion 33 and the flexible tube 32 and inserted into a body cavity. As illustrated in FIG. 3 or 4, the insertion portion 5 includes a flexible portion 51 which is a long tube having flexibility, and a distal end portion 52 and a bending portion 53 which will be described below.

The distal end portion 52 is constituted of an end effector such as a knife that treats a living tissue by applying treatment energy to the living tissue, forceps that grasp the living tissue, or others. Note that FIGS. 3 and 4 illustrate a case where the distal end portion 52 is configured by forceps.

The bending portion 53 is a tubular body configured to connect the distal end portion 52 and the tube 7 and to be bendable in a direction intersecting the central axis Ax.

The operating unit 6 is a portion operated by the surgical operator Y. As illustrated in FIG. 3 or 4, the operating unit 6 includes a first operating portion 61 and a second operating portion 62.

The first operating portion 61 is a portion which is provided on the proximal end side Ar2 of the flexible portion 51 and receives a bending operation for bending the distal end portion 52 (bending portion 53) from the surgical operator Y. As illustrated in FIG. 3 or 4, the first operating portion 61 includes a socket 611, a ball 612, and an operating handle 613.

The socket 611 has a shape in which a portion on the proximal end side Ar2 of a hollow sphere is cut out by a plane orthogonal to the central axis Ax, and has an opening 6111 (FIG. 4) on the proximal end side Ar2.

The ball 612 has a substantially spherical shape, is supported on the inner surface of the socket 611 in a state where the center of the ball 612 coincides with the center of the socket 611, and is configured to be rotatable in any direction about its center with respect to the socket 611. In other words, the first operating portion 61 is constituted of a so-called ball joint structure.

The operating handle 613 is a long member extending on a straight line from an outer surface of the ball 612 which is not covered with the socket 611, and is positioned on the central axis Ax in an initial state in which the distal end portion 52 is not bent. The operating handle 613 receives a bending operation from the surgical operator Y. The bending operation is an operation of tilting the operating handle 613 in any direction about the center of the socket 611 and the ball 612.

The second operating portion 62 is fixed to the outer surface on the proximal end side Ar2 of the flexible portion 51, and has an annular shape centered on the central axis Ax. The second operating portion 62 receives a rotation operation from the surgical operator Y. The rotation operation is an operation of rotating the second operating portion 62 about the central axis Ax. The rotation operation rotates the insertion portion 5 about the central axis Ax with respect to the first operating portion 61.

The tube 7 is provided inside the flexible portion 51 and is configured to be torsionally deformable around the central axis Ax. The outer peripheral surface of the end portion on the distal end side Ar1 of the tube 7 is fixed to the inner peripheral surface of the end portion of the flexible portion 51 on the distal end side Ar1 at a position P1 (FIG. 4). The end portion on the proximal end side Ar2 of the tube 7 is fixed to the end portion of the socket 611 on the distal end side Ar1 at a position P2 (FIG. 4). In other words, when a rotation operation is performed on the second operating portion 62 by the surgical operator Y, the tube 7 is twisted around the central axis Ax because the end portion on the distal end side Ar1 of the tube, together with the insertion portion 5, is rotated about the central axis Ax with respect to the end portion (first operating portion 61) on the proximal end side Ar2 of the tube.

In the first embodiment, the tube 7 is constituted of a so-called twisted multi-lumen tube. Specifically, the tube 7 has four through-holes 71 each penetrating from the proximal end to the distal end and each extending spirally along the central axis Ax. FIG. 4 illustrates only two through-holes 71.

The wire 8 is bridged between the distal end portion 52 and the first operating portion 61 (ball 612) in a state of being inserted through the through-hole 71, and transmits a force applied to the ball 612 in response to a bending operation to the distal end portion 52. In the first embodiment, four wires 8 are provided, the number of the wires of which is the same as that of the through-holes 71. FIG. 4 illustrates only two wires 8. One wire 8 of the four wires 8 (hereinafter referred to as an upper wire 8) has one end fixed to a +Z-axis side portion of the end surface on the proximal end side Ar2 of the distal end portion 52 and the other end fixed to the +Z-axis side outer surface of the ball 612 by the adjustment mechanism 9. Another one wire 8 of the wires (hereinafter referred to as a lower wire 8) has one end fixed to a −Z-axis side portion of the end surface on the proximal end side Ar2 of the distal end portion 52 and the other end fixed to a −Z-axis side outer surface of the ball 612 by the adjustment mechanism 9. Further, another one wire 8 of the wires (hereinafter referred to as a left wire 8) has one end fixed to a +Y-axis side portion of the end surface on the proximal end side Ar2 of the distal end portion 52 and the other end fixed to a +Y-axis side outer surface of the ball 612 by the adjustment mechanism 9. Another one wire 8 of the wires (hereinafter referred to as a right wire 8) has one end fixed to a −Y-axis side portion of the end surface on the proximal end side Ar2 of the distal end portion 52 and the other end fixed to a −Y-axis side outer surface of the ball 612 by the adjustment mechanism 9.

When the operating handle 613 is tilted in the Z-axis direction by the bending operation by the surgical operator Y, one wire 8 of the upper wire 8 and the lower wire 8 is pulled toward the proximal end side Ar2, and the other wire 8 is pushed toward the distal end side Ar1. Thus, the bending portion 53 is bent in the Z-axis direction. When the operating handle 613 is tilted in the Y-axis direction by the bending operation by the surgical operator Y, one wire 8 of the left wire 8 and the right wire 8 is pulled toward the proximal end side Ar2, and the other wire 8 is pushed toward the distal end side Ar1. Thus, the bending portion 53 is bent in the Y-axis direction.

Depending on the state of the flexible manipulator 4A, the tilting direction of the operating handle 613 may not coincide with the bending direction of the bending portion 53. In such a case, the surgical operator Y can match the tilting direction of the operating handle 613 with the bending direction of the bending portion 53 by performing a rotation operation on the second operating portion 62 and rotating the insertion portion 5 about the central axis Ax with respect to the first operating portion 61.

When the rotation operation is performed on the second operating portion 62, the tube 7 is twisted around the central axis Ax as described above. As a result, as described below, the state of the wire 8 wired laid between the proximal end of the tube 7 and the outer surface of the ball 612 changes.

Specifically, it is assumed that the spiral direction in the through-hole 71 is a clockwise spiral direction when viewed from the proximal end side Ar2 along the central axis Ax, and the second operating portion 62 is rotated clockwise which is a direction identical to the spiral direction in response to the rotation operation. In this case, the tube 7 is twisted around the central axis Ax, so that the path (through-hole 71) through which the wire 8 is inserted is shortened, and the wire 8 laid between the proximal end of the tube 7 and the outer surface of the ball 612 is loosened. In other words, when the second operating portion 62 is rotated in a direction identical to the spiral direction in the through-hole 71, the wire 8 laid between the proximal end of the tube 7 and the outer surface of the ball 612 is loosened.

On the other hand, it is assumed that the spiral direction in the through-hole 71 is a clockwise spiral direction when viewed from the proximal end side Ar2 along the central axis Ax, and the second operating portion 62 is rotated counterclockwise which is a direction opposite to the spiral direction in response to the rotation operation. In this case, the tube 7 is twisted around the central axis Ax, so that the path (through-hole 71) through which the wire 8 is inserted is lengthened, and excessive tension is applied to the wire 8 laid between the proximal end of the tube 7 and the outer surface of the ball 612. In other words, when the second operating portion 62 is rotated in a direction opposite to the spiral direction in the through-hole 71, excessive tension is applied to the wire 8 laid between the proximal end of the tube 7 and the outer surface of the ball 612.

The adjustment mechanism 9 adjusts loosening or excessive tension generated in the wire 8 laid between the proximal end of the tube 7 and the outer surface of the ball 612.

[Configuration of Adjustment Mechanism]

Figure 5:
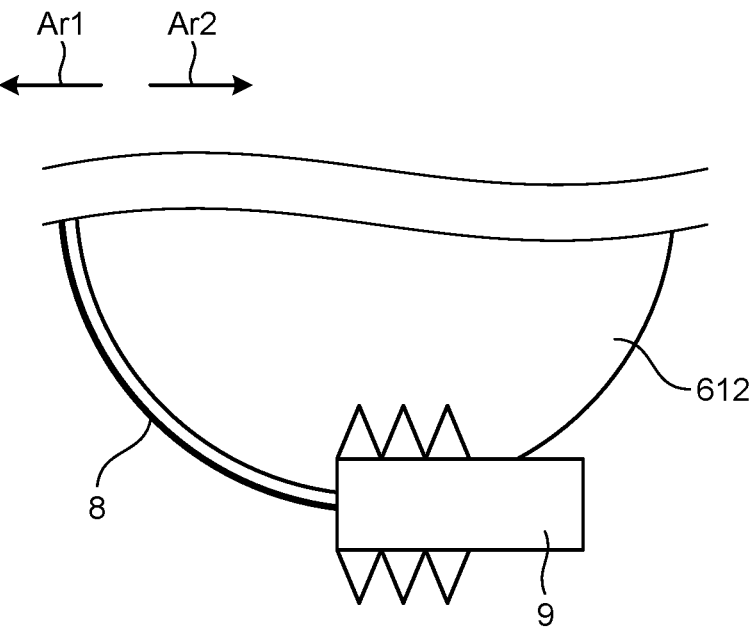
FIG. 5 is a diagram illustrating a configuration of an adjustment mechanism.

FIG. 5 is a diagram illustrating the configuration of the adjustment mechanism 9. Specifically, FIG. 5 is an enlarged view of a part of FIG. 4.

As illustrated in FIG. 5, the adjustment mechanism 9 is a screw to which the other end of the wire 8 is fixed and which is screwed into the ball 612. In other words, in the first embodiment, four adjustment mechanisms 9 are provided, the number of the adjustment mechanisms of which is the same as that of the wires 8.

The adjustment mechanism 9 reduces the amount of loosening generated in the wire 8 laid between the proximal end of the tube 7 and the outer surface of the ball 612 by an operator such as the surgical operator Y changing the screwed state with the ball 612 and moving the adjustment mechanism to the proximal end side Ar2.

On the other hand, the adjustment mechanism 9 reduces the excessive tension generated in the wire 8 laid between the proximal end of the tube 7 and the outer surface of the ball 612 by the operator such as the surgical operator Y changing the screwed state with the ball 612 and moving the adjustment mechanism to the distal end side Ar1.

As described above, the adjustment mechanism 9 according to the first embodiment has a structure that is not interlocked with the rotation of the second operating portion 62.

According to the first embodiment described above, the following effects are obtained.

The flexible manipulator 4A according to the first embodiment includes the adjustment mechanism 9 described above. Thus, loosening and excessive tension generated in the wire 8 laid between the proximal end of the tube 7 and the outer surface of the ball 612 in response to the rotation operation can be reduced by the adjustment mechanism 9.

Therefore, the flexible manipulator 4A according to the first embodiment can stabilize the operability.

In particular, the adjustment mechanism 9 is constituted of a screw. Thus, the operability can be stabilized with a simple structure.

Second Embodiment

A second embodiment will now be described.

In the following description, the same components as those of the first embodiment described above are denoted by the same reference numerals, and detailed description thereof will be omitted or simplified.

The second embodiment is different from the first embodiment described above in the configuration of the adjustment mechanism 9. The adjustment mechanism according to the second embodiment is hereinafter referred to as an adjustment mechanism 9A for convenience of description.

Figure 6:
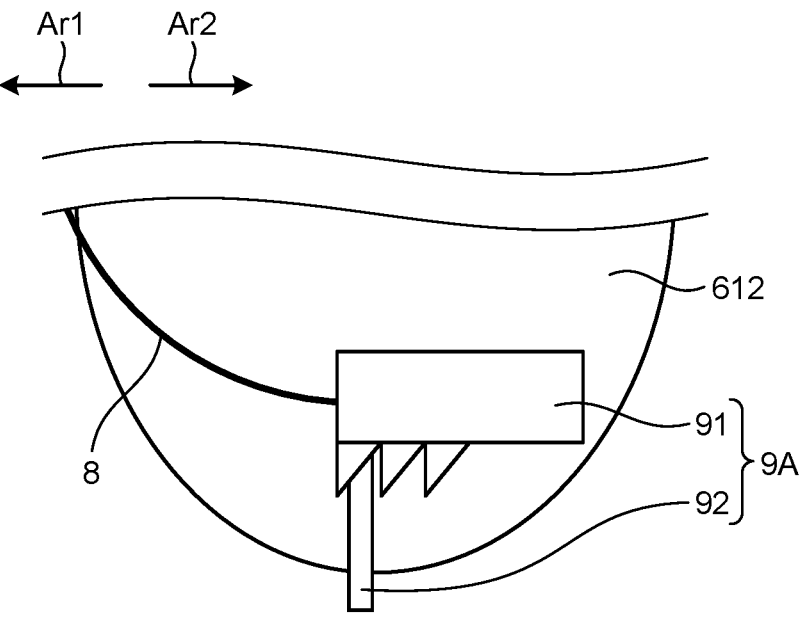
FIG. 6 is a diagram illustrating a configuration of an adjustment mechanism according to a second embodiment.

FIG. 6 is a diagram illustrating the configuration of the adjustment mechanism 9A according to the second embodiment. Specifically, FIG. 6 is a diagram corresponding to FIG. 5.

As illustrated in FIG. 6, the adjustment mechanism 9A is constituted of a ratchet having an advancing/retracting member 91 and a regulating member 92.

The advancing/retracting member 91 is fixed to the other end of the wire 8, and is attached to the ball 612 so as to be capable of advancing and retracting along the central axis Ax.

The regulating member 92 is configured to be movable in a direction orthogonal to the central axis Ax in response to a user operation by the surgical operator Y, and regulates the position of the advancing/retracting member 91 by engaging with the advancing/retracting member 91.

The adjustment mechanism 9A reduces the amount of loosening generated in the wire 8 laid between the proximal end of the tube 7 and the outer surface of the ball 612 by the operator such as the surgical operator Y moving the position of the advancing/retracting member 91 to the proximal end side Ar2.

On the other hand, the adjustment mechanism 9A reduces the excessive tension generated in the wire 8 laid between the proximal end of the tube 7 and the outer surface of the ball 612 by the operator such as the surgical operator Y moving the position of the advancing/retracting member 91 to the distal end side Ar1.

As described above, the adjustment mechanism 9A has a structure that is not interlocked with the rotation of the second operating portion 62 as in the adjustment mechanism 9 according to the first embodiment described above.

Even when the adjustment mechanism 9A according to the second embodiment described above is employed, the same effects as those of the first embodiment described above are obtained.

Third Embodiment

A third embodiment will now be described.

In the following description, the same components as those of the first embodiment described above are denoted by the same reference numerals, and detailed description thereof will be omitted or simplified.

The third embodiment is different from the first embodiment described above in the configuration of the adjustment mechanism 9. The adjustment mechanism according to the third embodiment is hereinafter referred to as an adjustment mechanism 9B for convenience of description.

Figure 7:
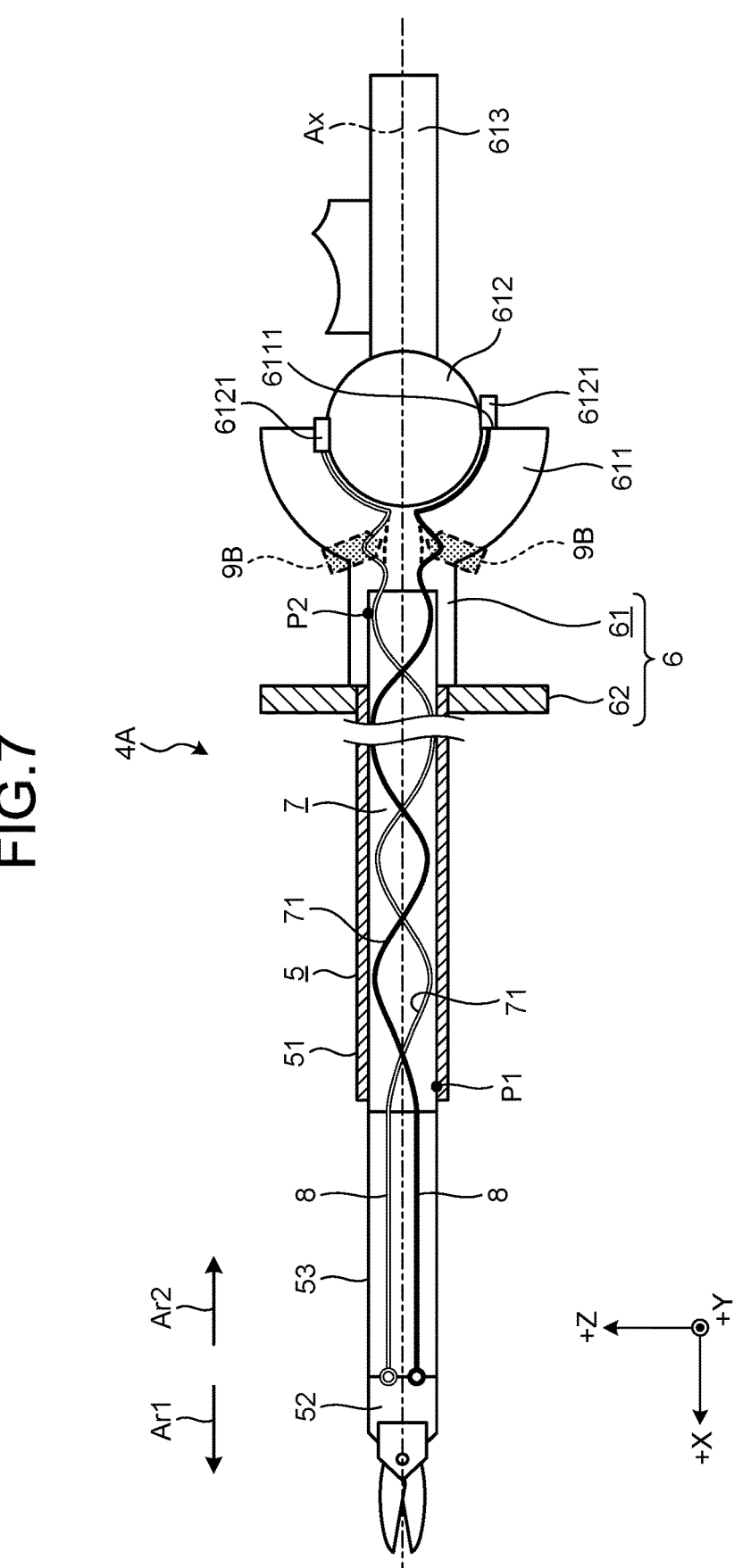
FIG. 7 is a diagram for explaining a configuration of an adjustment mechanism according to a third embodiment.

FIG. 7 is a diagram for explaining the configuration of the adjustment mechanism 9B according to the third embodiment. Specifically, FIG. 7 is a diagram corresponding to FIG. 4.

As illustrated in FIG. 7, the wire 8 has the other end fixed to the outer surface of the ball 612 by a fixing member 6121. The fixing member 6121 is fixed to the outer surface of the ball 612.

As illustrated in FIG. 7, the adjustment mechanism 9B is a bar which is attached to the socket 611 so as to be capable of advancing and retracting between the inside and outside of the socket 611 and whose distal end portion is in contact with the wire 8 laid between the proximal end of the tube 7 and the outer surface of the ball 612.

The adjustment mechanism 9B has a distal end portion pressed against the wire 8 laid between the proximal end of the tube 7 and the outer surface of the ball 612 by the operator such as the surgical operator Y moving the adjustment mechanism 9B toward the inside of the socket 611. Thus, the amount of loosening generated in the wire 8 is reduced.

On the other hand, the adjustment mechanism 9B reduces the force in which a distal end portion thereof is pressed against the wire 8 laid between the proximal end of the tube 7 and the outer surface of the ball 612, by the operator such as the surgical operator Y moving the adjustment mechanism 9B toward the outside of the socket 611. Thus, excessive tension generated in the wire 8 is reduced.

As described above, the adjustment mechanism 9B has a structure that is not interlocked with the rotation of the second operating portion 62 as in the adjustment mechanism 9 according to the first embodiment described above.

The adjustment mechanism 9B described above can be exemplified by a set screw.

Even when the adjustment mechanism 9B according to the third embodiment described above is employed, the same effects as those of the first embodiment described above are obtained.

Fourth Embodiment

A fourth embodiment will now be described.

In the following description, the same components as those of the first embodiment described above are denoted by the same reference numerals, and detailed description thereof will be omitted or simplified.

The fourth embodiment is different from the first embodiment described above in the configuration of the adjustment mechanism 9. The adjustment mechanism according to the fourth embodiment is hereinafter referred to as an adjustment mechanism 9C for convenience of description. In the fourth embodiment, the second operating portion 62 described in the first embodiment described above is omitted.

Figure 8:
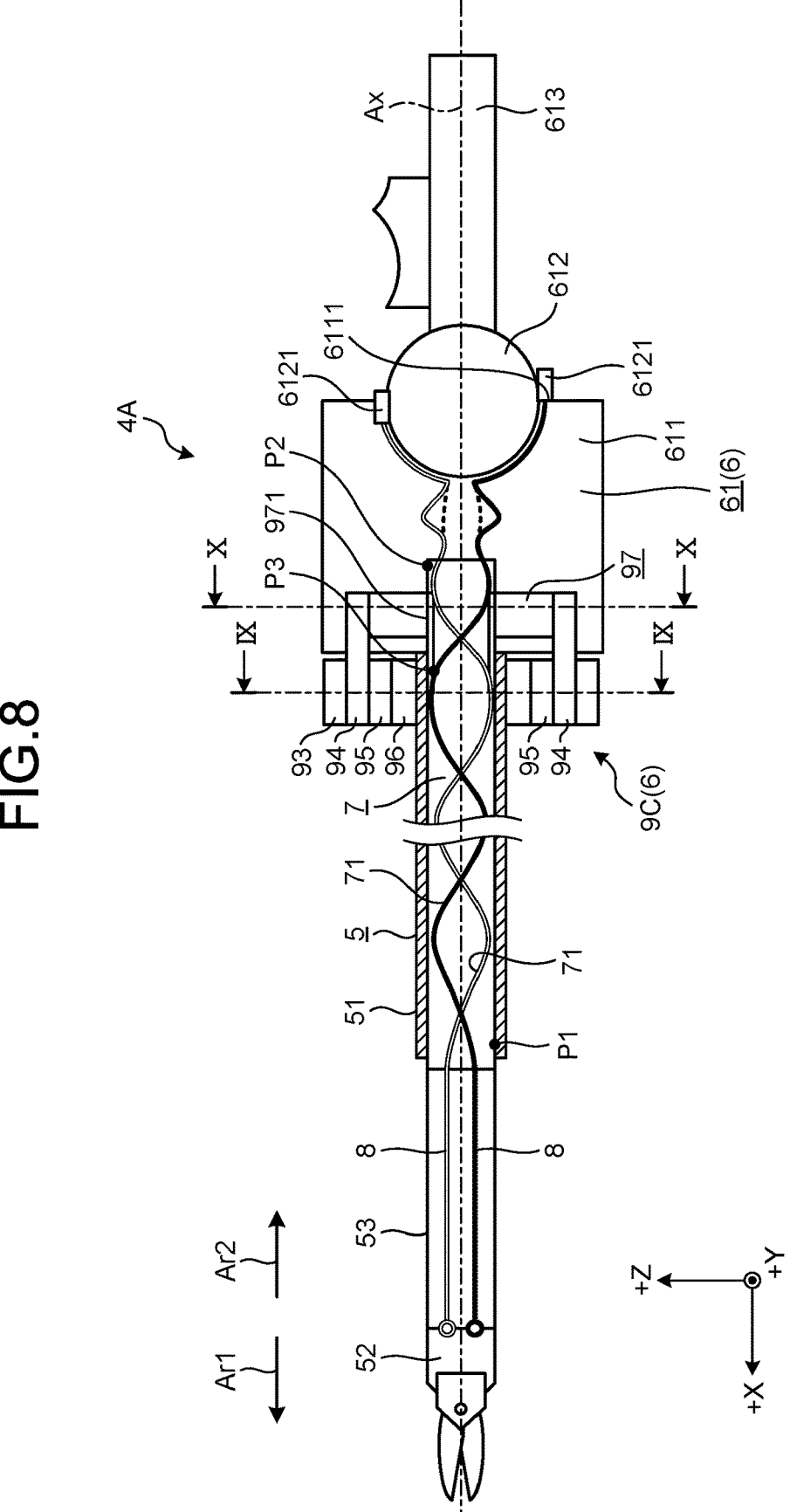
FIG. 8 is a diagram for explaining a configuration of an adjustment mechanism according to a fourth embodiment.
Figure 9:
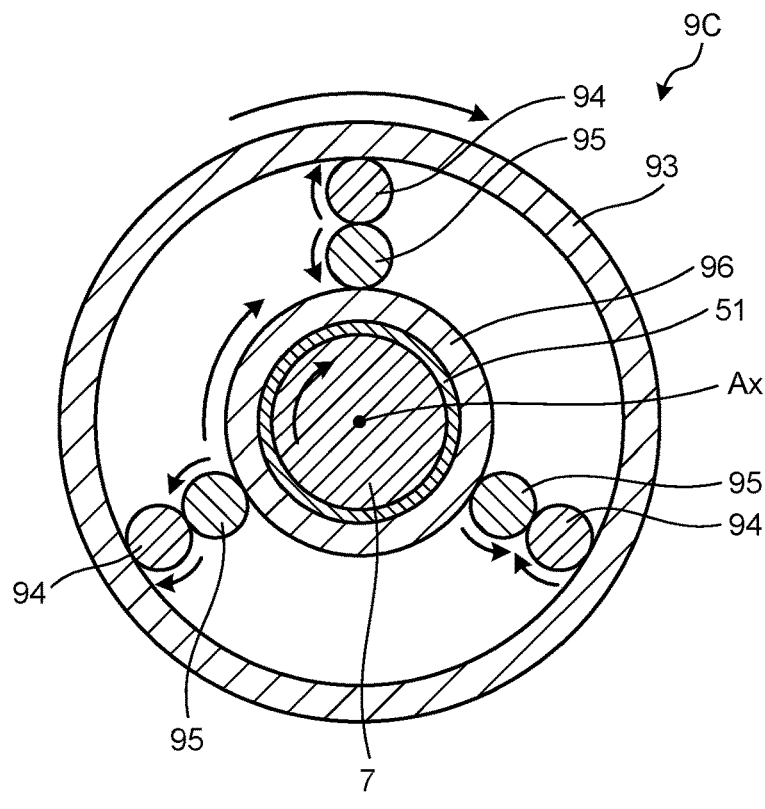
FIG. 9 is a diagram for explaining the configuration of the adjustment mechanism according to the fourth embodiment.
Figure 10:
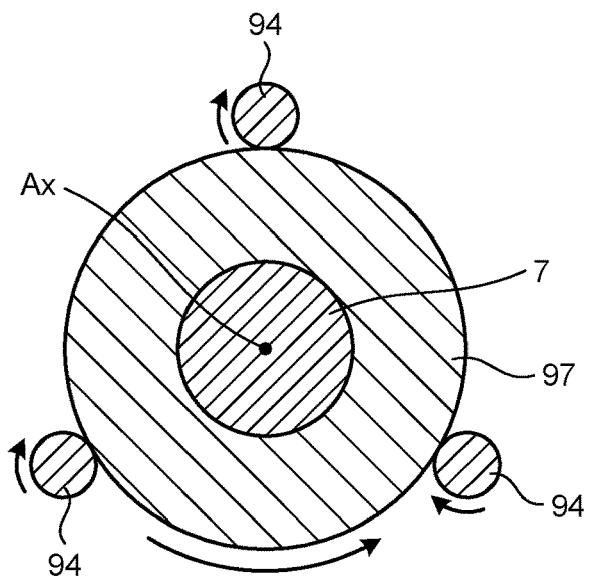
FIG. 10 is a diagram for explaining the configuration of the adjustment mechanism according to the fourth embodiment.

FIGS. 8 to 10 are diagrams for explaining the configuration of the adjustment mechanism 9C according to the fourth embodiment. Specifically, FIG. 8 is a diagram corresponding to FIG. 4. FIG. 9 is a cross-sectional view taken along line IX-IX of FIG. 8. FIG. 10 is a cross-sectional view taken along line X-X of FIG. 8.

As illustrated in FIG. 8, the wire 8 has the other end fixed to the outer surface of the ball 612 by the fixing member 6121 as in the third embodiment described above.

As illustrated in FIGS. 8 to 10, the adjustment mechanism 9C includes an internal gear 93, three first planetary gears 94, three second planetary gears 95, a first sun gear 96, and a second sun gear 97.

The internal gear 93 is an annular internal gear centered on the central axis Ax, and receives a rotation operation from the surgical operator Y. In other words, the internal gear 93 also has a function as the second operating portion according to the present disclosure.

As illustrated in FIG. 9, the three first planetary gears 94 are disposed inside the internal gear 93 at a position to be rotationally symmetric by 120° about the central axis Ax. The three first planetary gears 94 each mesh with the internal gear 93 while being each rotatably supported with respect to the socket 611.

As illustrated in FIG. 9, the three second planetary gears 95 are each disposed inside the internal gear 93 at a position to be rotationally symmetric by 120° about the central axis Ax and at a position closer to the central axis Ax than the three first planetary gears 94. The three second planetary gears 95 each mesh with the three first planetary gears 94 while being each rotatably supported with respect to the sockets 611.

The first sun gear 96 is an external gear having an annular shape centered on the central axis Ax, and as illustrated in FIG. 9, is fixed to the outer surface on the proximal end side Ar2 of the flexible portion 51 inside the internal gear 93. The first sun gear 96 meshes with the three second planetary gears 95.

The second sun gear 97 is an external gear having an annular shape centered on the central axis Ax, and as illustrated in FIG. 8, is positioned closer to the proximal end side Ar2 than the internal gear 93, and is disposed inside the socket 611. The second sun gear 97 meshes with the three first planetary gears 94, as illustrated in FIG. 9.

As illustrated in FIG. 8, the second sun gear 97 has an inner peripheral edge provided with a connection portion 971 extending toward the distal end side Ar1. The connection portion 971 has a cylindrical shape centered on the central axis Ax. The inner peripheral surface on the distal end side Ar1 of the connection portion 971 is fixed at a position P3 (FIG. 8) spaced apart from the proximal end of the tube 7 toward the distal end side Ar1 on the outer peripheral surface of the tube 7.

The adjustment mechanism 9C operates as follows. Note that the clockwise and the counterclockwise directions described below mean directions viewed from the proximal end side Ar2.

For example, as indicated by an arrow in FIG. 9, when the internal gear 93 is rotated clockwise about the central axis Ax by a rotation operation from the surgical operator Y, the three first planetary gears 94 are also rotated clockwise. The three second planetary gears 95 are each rotated counterclockwise in accordance with the rotation of the three first planetary gears 94. The first sun gear 96 is rotated clockwise about the central axis Ax together with the insertion portion 5 in accordance with the rotation of the three second planetary gears 95. On the other hand, as indicated by an arrow in FIG. 10, the second sun gear 97 is rotated counterclockwise about the central axis Ax together with the position P3 of the tube 7 in accordance with the rotation of the three first planetary gears 94.

As described above, the adjustment mechanism 9C has a structure that is interlocked with the rotation operation and has a function of canceling the twisting of the tube 7 caused by the rotation operation. Note that although FIGS. 9 and 10 illustrate the case where the internal gear 93 rotates clockwise when viewed from the proximal end side Ar2, even when the internal gear rotates counterclockwise, the adjustment mechanism 9C cancels the twisting of the tube 7 caused by the rotation operation.

Even when the adjustment mechanism 9C according to the fourth embodiment described above is employed, the same effects as those of the first embodiment described above are obtained.

Fifth Embodiment

A fifth embodiment will now be described.

In the following description, the same components as those of the first embodiment described above are denoted by the same reference numerals, and detailed description thereof will be omitted or simplified.

The fifth embodiment is different from the first embodiment described above in the configuration of the adjustment mechanism 9. The adjustment mechanism according to the fifth embodiment is hereinafter referred to as an adjustment mechanism 9D for convenience of description. In the fifth embodiment, the second operating portion 62 described in the first embodiment described above is omitted.

Figure 11:
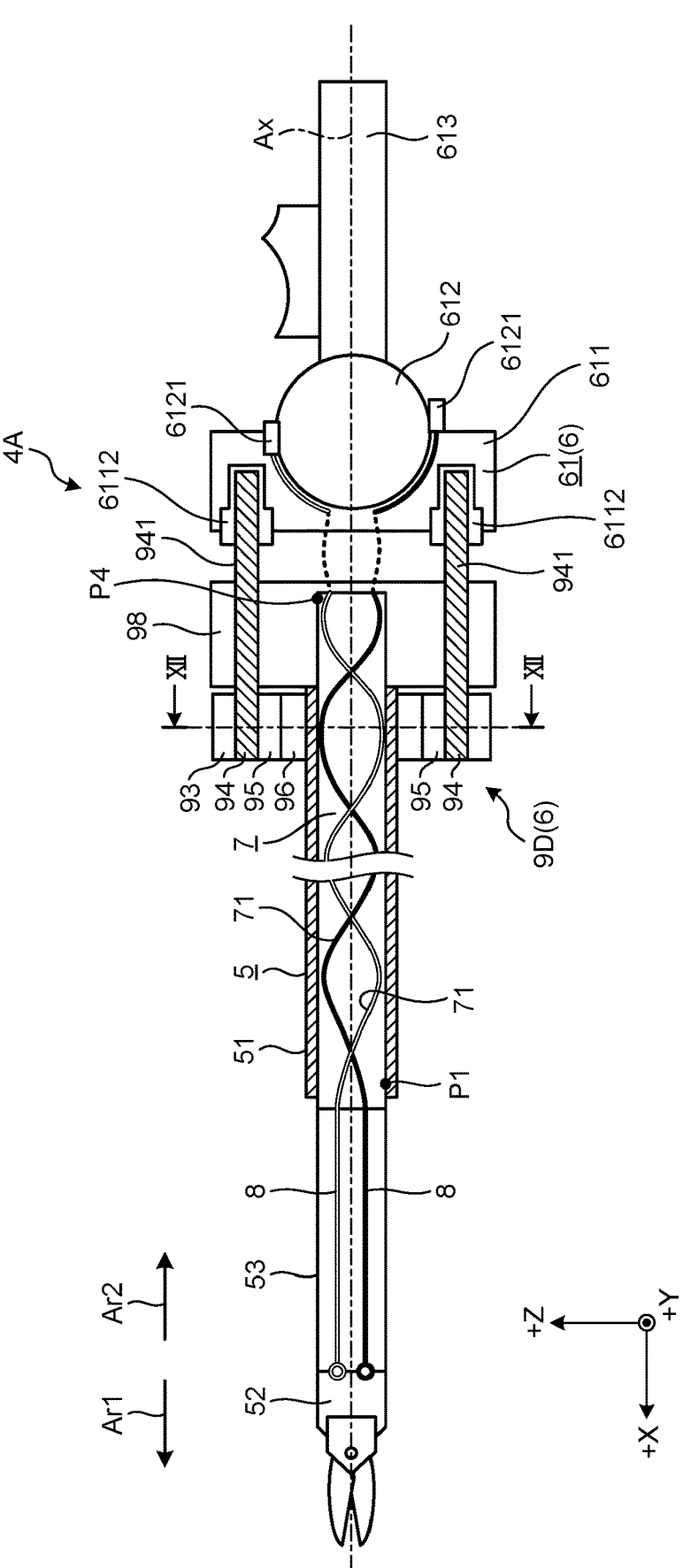
FIG. 11 is a diagram for explaining a configuration of an adjustment mechanism according to a fifth embodiment.
Figure 12:
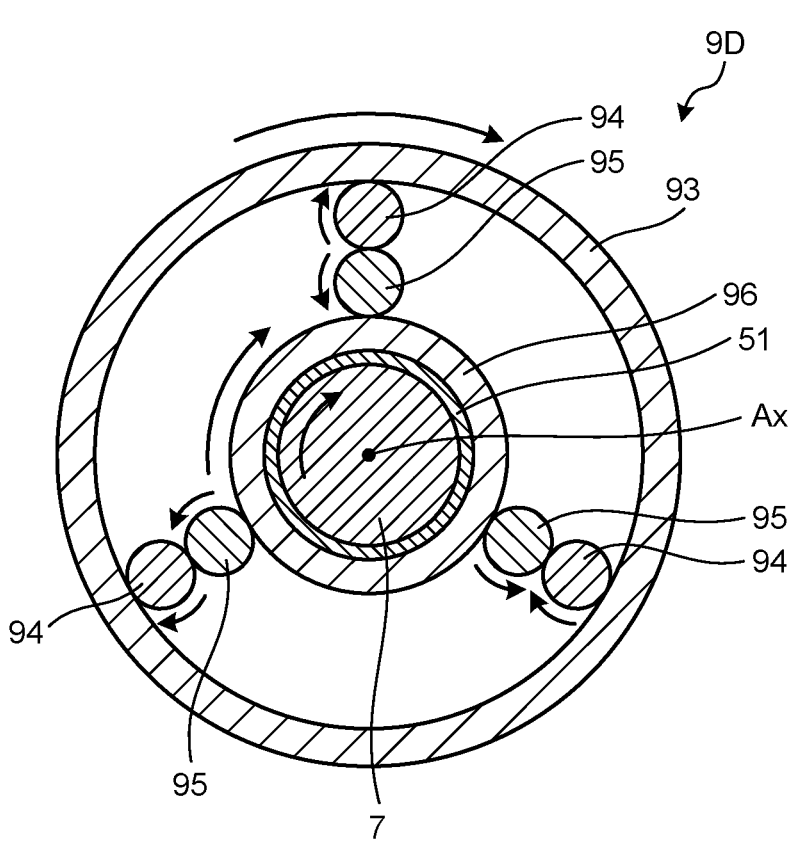
FIG. 12 is a diagram for explaining a configuration of an adjustment mechanism according to a fifth embodiment.

FIGS. 11 and 12 are diagrams for explaining the configuration of the adjustment mechanism 9D according to the fifth embodiment. Specifically, FIG. 11 is a diagram corresponding to FIG. 4. FIG. 12 is a cross-sectional view taken along line XII-XII of FIG. 11.

As illustrated in FIG. 11, the wire 8 has the other end fixed to the outer surface of the ball 612 by the fixing member 6121 as in the third embodiment described above.

The adjustment mechanism 9D has a structure that is interlocked with the rotation operation as in the fourth embodiment described above. As illustrated in FIG. 11 or 12, the adjustment mechanism 9D includes a base body 98 in addition to the internal gear 93, the three first planetary gears 94, the three second planetary gears 95, and the first sun gear 96 described in the fourth embodiment described above.

As illustrate in FIG. 11, the three first planetary gears 94 according to the fifth embodiment are each provided with a screw shaft 941 linearly extending toward the proximal end side Ar2.

The screw shaft 941 penetrates the base body 98. The end portion on the proximal end side Ar2 of the screw shaft 941 is screwed into a nut 6112 provided in the socket 611. In the fifth embodiment, the screw shaft 941 and the nut 6112 are constituted of a so-called ball screw.

The three second planetary gears 95 according to the fifth embodiment are each rotatably supported not with respect to the socket 611 but with respect to the base body 98.

The base body 98 has an annular shape centered on the central axis Ax, and is positioned between the internal gear

93 and the socket 611 as illustrated in FIG. 11. The tube 7 has an outer peripheral surface fixed to the inner peripheral edge of the base body 98 at a position P4. Note that, in the fifth embodiment, the tube 7 is not fixed to the socket 611.

The adjustment mechanism 9D operates as follows. Note that the clockwise and the counterclockwise directions described below mean directions viewed from the proximal end side Ar2.

In the following, it is assumed that the spiral direction in the through-hole 71 is a clockwise spiral direction.

For example, as indicated by an arrow in FIG. 12, when the internal gear 93 is rotated clockwise, which is a direction identical to the spiral direction in the through-hole 71, about the central axis Ax by a rotation operation from the surgical operator Y, the three first planetary gears 94 are also rotated clockwise. The three second planetary gears 95 are each rotated counterclockwise in accordance with the rotation of the three first planetary gears 94. The first sun gear 96 is rotated clockwise about the central axis Ax together with the insertion portion 5 in accordance with the rotation of the three second planetary gears 95.

In other words, in the above case, the tube 7 is twisted around the central axis Ax, so that the path (through-hole 71) through which the wire 8 is inserted is shortened, and the wire 8 laid between the proximal end of the tube 7 and the outer surface of the ball 612 is loosened.

On the other hand, in accordance with the rotation of the three first planetary gears 94 (screw shafts 941), the screwed state between the screw shafts 941 and the nuts 6112 is changed, and thus the first operating portion 61 moves toward the proximal end side Ar2 from the base body 98. Thus, the amount of loosening generated in the wire 8 laid between the proximal end of the tube 7 and the outer surface of the ball 612 is reduced.

Note that, in the fifth embodiment, a movement amount M1 (a linear motion amount by the ball screw (screw shaft 941 and nut 6112)) by which the first operating portion 61 is separated from the base body 98 when the internal gear 93 is rotated once around the central axis Ax is set as illustrated in the following Equation 1. In Equation 1, d means a diameter of a circle formed by the through-hole 71 when the spiral through-hole 71 is viewed along the central axis Ax. p means a length (twist pitch) along the central axis Ax when the spiral through-hole 71 is rotated once around the central axis Ax. The first term on the right side in Equation 1 means the length per rotation around the central axis Ax in the spiral through-hole 71. In other words, the right side in Equation 1 corresponds to the amount of loosening generated in the wire 8 laid between the proximal end of the tube 7 and the outer surface of the ball 612 when the internal gear 93 is rotated once around the central axis Ax.

$$M1 = \sqrt{(d\pi)^2 + p^2} - p \tag{1}$$

In contrast to the above, when the internal gear 93 is rotated counterclockwise, the tube 7 is twisted around the central axis Ax, so that the path (through-hole 71) through which the wire 8 is inserted is lengthened, and excessive tension is applied to the wire 8 laid between the proximal end of the tube 7 and the outer surface of the ball 612. In accordance with the rotation of the three first planetary gears 94 (screw shafts 941), the screwed state between the screw shafts 941 and the nuts 6112 is changed, and thus the first operating portion 61 moves toward the distal end side Ar1 close to the base body 98. Thus, excessive tension generated in the wire 8 laid between the proximal end of the tube 7 and the outer surface of the ball 612 is reduced.

Even when the adjustment mechanism 9D according to the fifth embodiment described above is employed, the same effects as those of the first embodiment described above are obtained.

OTHER EMBODIMENTS

While the embodiments for carrying out the present disclosure have been described above, the present disclosure should not be limited only to the first to fifth embodiments described above.

Although the number of the through-holes 71 formed in the tube 7 is four in the first to fifth embodiments described above, the number of the through-holes 71 is not limited to four and may be two, three, or five or more.

The adjustment mechanism 9B according to the third embodiment described above is not limited to a set screw, and may be configured by a ratchet mechanism as in the adjustment mechanism 9A according to the second embodiment.

REFERENCE SIGNS LIST

1 MEDICAL MANIPULATOR SYSTEM
2 ENDOSCOPE
3 ACCESS DEVICE
4A, 4B FLEXIBLE MANIPULATOR
5 INSERTION PORTION
6 OPERATING UNIT
7 TUBE
8 WIRE
9, 9A to 9D ADJUSTMENT MECHANISM
31 ENDO SCOPE MOUNTING PORTION
32 FLEXIBLE TUBE
33 RIGID TUBULAR PORTION
34 FIXING PORTION
51 FLEXIBLE PORTION
52 DISTAL END PORTION
53 BENDING PORTION
61 FIRST OPERATING PORTION
62 SECOND OPERATING PORTION
71 THROUGH-HOLE
91 ADVANCING/RETRACTING MEMBER
92 REGULATING MEMBER
93 INTERNAL GEAR
94 FIRST PLANETARY GEAR
95 SECOND PLANETARY GEAR
96 FIRST SUN GEAR
97 SECOND SUN GEAR
98 BASE BODY
311 FIRST MOUNTING HOLE
312 SECOND MOUNTING HOLE
611 SOCKET
612 BALL
613 OPERATING HANDLE
941 SCREW SHAFT
971 CONNECTION PORTION
6111 OPENING
6112 NUT
6121 FIXING MEMBER
Ar1 DISTAL END SIDE
Ar2 PROXIMAL END SIDE
Ax CENTRAL AXIS
D DISPLAY
OT OPERATING TABLE
P1 to P4 POSITION
S SCOPIST

X PATIENT
Y SURGICAL OPERATOR

What is claimed is:

1. A flexible manipulator, comprising:
an insertion portion including a tubular flexible portion, a bending portion, and a distal end portion;
an operating unit on a proximal end side of the insertion portion, the operating unit including a first operating portion;
a tube inside the tubular flexible portion, the tube including a through-hole spirally extending along a longitudinal axis of the tube from a proximal end to a distal end; and
a wire extending through the through-hole, a first end of the wire connected to the distal end portion and a second end of the wire connected to the first operating portion,
wherein the first operating portion includes an adjustment mechanism,
wherein the bending portion is a tubular body between the distal end portion and a distal end side of the tube,
wherein the flexible manipulator is configured such that operation of the first operating portion transmits a force applied to the first operating portion via the wire to the distal end portion to bend the bending portion relative to a central axis of the insertion portion,
wherein the adjustment mechanism adjusts a tension in the wire, and
wherein an outer surface of the distal end of the tube is attached to an inner surface of the end portion of the tubular flexible portion.

2. The flexible manipulator according to claim 1, wherein the adjustment mechanism includes a first adjustment mechanism that is movable proximally and distally relative to the central axis of the insertion portion and the first adjustment mechanism adjusts the tension in the wire by moving proximally or distally relative to the central axis of the insertion portion.

3. The flexible manipulator according to claim 2, wherein the first adjustment mechanism is a screw, wherein the screw is fixed to the second end of the wire, and wherein the screw is threaded into the first operating portion.

4. The flexible manipulator according to claim 2, wherein the first adjustment mechanism is a ratchet, wherein the ratchet is fixed to the second end of the wire, and wherein the ratchet is attached to the first operating portion.

5. The flexible manipulator according to claim 1, wherein the adjustment mechanism includes a first adjustment mechanism, wherein the first adjustment mechanism is a bar that contacts the wire and is movable to advance and retract between an inside and an outside of the first operating portion, and wherein the first adjustment mechanism adjusts the tension in the wire by advancing or retracting between the inside and the outside of the first operating portion.

6. The flexible manipulator according to claim 1, wherein the adjustment mechanism includes a first adjustment mechanism and a second adjustment mechanism,
wherein the first adjustment mechanism is movable proximally and distally relative to the central axis of the insertion portion and the first adjustment mechanism adjusts the tension in the wire by moving proximally or distally relative to the central axis of the insertion portion,
wherein the operating unit further comprises a second operating portion and the second operating portion includes the second adjustment mechanism, wherein the second adjustment mechanism is rotatable about the central axis of the insertion portion to rotate the flexible portion and the distal end portion about a central axis of the flexible portion and relative to the first operating portion, and wherein the second adjustment mechanism adjusts the tension in the wire by rotating the flexible portion and the distal end portion about the central axis of the flexible portion and relative to the first operating portion.

7. The flexible manipulator according to claim 6, wherein the first adjustment mechanism is not interlocked with a rotation of the second operating portion.

8. The flexible manipulator according to claim 7, wherein the first adjustment mechanism is a screw, wherein the screw is fixed to the second end of the wire, and wherein the screw is threaded into the first operating portion.

9. The flexible manipulator according to claim 7, wherein the first adjustment mechanism is a ratchet, wherein the ratchet is fixed to the second end of the wire, and wherein the ratchet is attached to the first operating portion.

10. The flexible manipulator according to claim 6, wherein the second adjustment mechanism includes an internal gear, a plurality of first planetary gears, a plurality of second planetary gears, and a plurality of sun gears.

11. The flexible manipulator according to claim 10, wherein the internal gear has an annular shape and centered on the central axis of the insertion portion, wherein the plurality of first planetary gears is disposed inside the internal gear at a position rotationally symmetric by 120° about the central axis of the insertion portion, and the plurality of first planetary gears mesh with the internal gear, wherein the plurality of second planetary gears is disposed inside the internal gear at a position to be rotationally symmetric by 120° about the central axis of the insertion portion and at a position radially closer to the central axis of the insertion portion than the plurality of first planetary gears, and the plurality of second planetary gears mesh with the plurality of first planetary gears, wherein a first sun gear of the plurality of sun gears is an annular-shaped gear disposed inside the internal gear and is centered on the central axis of the insertion portion, the first sun gear fixed to an outer surface of a proximal end side of the flexible tubular portion and meshes with the plurality of second planetary gears, and wherein a second sun gear of the plurality of sun gears is an annular-shaped gear disposed inside the internal gear and is centered on the central axis of the insertion portion, the second sun gear axially offset from the first sun gear and meshes with the plurality of first planetary gears.

12. The flexible manipulator according to claim 1, wherein the adjustment mechanism includes a first adjustment mechanism and a second adjustment mechanism, wherein the first adjustment mechanism adjusts the tension in the wire by advancing or retracting between an inside and an outside of the first operating portion, wherein the operating unit further comprises a second operating portion and the second operating portion includes the second adjustment mechanism, wherein the second adjustment mechanism is rotatable about the central axis of the insertion portion to rotate the flexible portion and the distal end portion about a central axis of the flexible portion and relative to the first operating portion, and wherein the second adjustment mechanism adjusts the tension in the wire by rotating the flexible portion and the distal end portion about the central axis of the flexible portion and relative to the first operating portion.

13. The flexible manipulator according to claim 12, wherein the second adjustment mechanism is interlocked with a rotation of the second operating portion to rotate the proximal end side of the tube in a direction opposite to a rotation direction of the second operating portion.

14. The flexible manipulator according to claim 12, wherein the second adjustment mechanism is interlocked with a rotation of the second operating portion so that the first operating portion moves toward the second operating portion.

15. The flexible manipulator according to claim 12, wherein the first adjustment mechanism is not interlocked with a rotation of the second operating portion.

16. The flexible manipulator according to claim 1, wherein the operating unit further comprises a second operating portion, wherein the second operating portion rotates the flexible portion and the distal end portion about a central axis of the flexible portion and relative to the first operating portion.

17. The flexible manipulator according to claim 16, wherein the second operating portion includes the adjustment mechanism.

18. The flexible manipulator according to claim 17, wherein the second operating portion is between the flexible portion and the first operating portion.

19. The flexible manipulator according to claim 1, wherein the adjustment mechanism adjusts a tension in the wire by at least one of (i) loosening of the wire and (ii) tightening of the wire.

20. The flexible manipulator according to claim 1, wherein a first operating portion comprises a socket, a ball, and a handle, wherein the socket movably supports the ball, and wherein the handle is mounted on the ball.

21. The flexible manipulator according to claim 20, wherein the distal end portion includes an end effector, and wherein the bending portion bends relative to the central axis of the insertion portion in a direction intersecting the central axis of the insertion portion.

22. The flexible manipulator according to claim 1, wherein the adjustment mechanism contacts a portion of the wire located between a proximal end of the tube and the first operating portion.

23. The flexible manipulator according to claim 1, wherein the proximal end of the tube is fixed to the first operating portion.

24. The flexible manipulator according to claim 1, wherein the adjustment mechanism includes a first adjustment mechanism, wherein the first adjustment mechanism is a ratchet, wherein the ratchet includes an advancing/retracting member and a regulating member, wherein the advancing/retracting member is fixed to the second end of the wire and is movable proximally and distally relative to the central axis of the insertion portion, and wherein the regulating member is movable in a direction orthogonal to the central axis of the insertion portion.

25. The flexible manipulator according to claim 1, wherein the tube is torsionally deformable around a central axis of the tubular flexible portion.

\* \* \* \* \*